United States Patent [19]

Johnson et al.

[11] 4,133,717

[45] Jan. 9, 1979

[54] PROTEIN-FREE NUTRIENT MEDIUM

[75] Inventors: Russell C. Johnson; Russell F. Bey, both of Roseville, Minn.

[73] Assignee: The Regents of the University of Minnesota, Minneapolis, Minn.

[21] Appl. No.: 820,737

[22] Filed: Aug. 1, 1977

[51] Int. Cl.² .............................................. C12K 1/10
[52] U.S. Cl. .................................. 195/100; 195/102; 260/347.4; 195/96
[58] Field of Search ................. 195/99, 100, 101, 102, 195/103; 260/347.4

[56] References Cited

U.S. PATENT DOCUMENTS 3,816,261  6/1974  Torney .......................... 195/100 X

*Primary Examiner*—Alvin Tanenholtz
*Assistant Examiner*—Robert J. Warden
*Attorney, Agent, or Firm*—Burd, Braddock & Bartz

[57] ABSTRACT

A process for the preparation of a special protein-free nutrient medium having unexpected efficiency in the propagation of Leptospira. The process comprises strategically admixing a modified or detoxified polysorbate fatty acid to a preformed mixture containing vitamin $B_{12}$, vitamin $B_1$, soluble manganese, magnesium and ammonium salts, and a buffer, in a water diluent adjusted to pH 6.5 to 8.5. The polysorbate fatty acid is modified or detoxified by admixture with activated charcoal followed by settling, decantation, centrifugation and filtration to remove all charcoal particles.

13 Claims, No Drawings

PROTEIN-FREE NUTRIENT MEDIUM

The invention described herein was made in part in the course of work under a grant or award from the Department of Health, Education and Welfare.

This invention relates to the propagation of Leptospira and more particularly to the preparation of a special protein-free nutrient medium having unexpected efficiency in the propagation of Leptospira.

Leptospirosis, a communicable and sometimes fatal disease of humans and animals, is known to be transmitted from carrier to host by members of the spirochete genus Leptospira. Currently, the best known method of controlling leptospirosis is by the use of leptospiral vaccines. These vaccines contain inactivated leptospire cells or components of these cells.

In the present state of the art, the preparation of Leptospira vaccines generally comprises the method of: introducing Leptospira, taken from either a diseased host or Leptospira culture, into nutrient medium containing specific organic and inorganic components found necessary for the efficient growth of Leptospira, allowing the Leptospira to propagate in the medium, inactivating the Leptospira, and processing the inactivated culture into a pharmaceutically acceptable vaccine.

The nutrient composition of culture medium is especially vital for the rapid and homogeneous growth of Leptospira. Presently, it is believed that such culture media must contain a buffer, inorganic salts, vitamins, and a source of fatty acid to be operative.

One of the most efficient and economically acceptable sources of fatty acid now being used is the water-soluble lipid. Of the water-solid lipids, the polysorbates appear to be the preferred fatty acid source for Leptospira nutrient medium, especially the polyalkylene derivative of a sorbitol monoester of a fatty acid having from 12 to 20 carbon atoms. Such polysorbates are commercially available (e.g. Tween polysorbates from ICI America, Inc.).

As used herein, Tween 20 is used to designate a polyalkylene derivative of sorbitan monolaurate; Tween 40, a polyalkylene derivative of sorbitan monopalmitate; Tween 60, a polyalkylene derivative of sorbitan monostearate; and Tween 80, a polyalkylene derivative of sorbitan monooleate.

The use of the Tween and Tween-related compounds as nutrient components to produce a protein-free Leptospira culture medium have heretofore been restricted by the presence of toxic impurities in the commercially available Tween products and currently practiced methods of ameliorating the side effects of the toxic impurities have met only limited success.

One of the most effective methods thus far found is the addition of mammal blood serum or blood serum fractions to the nutrient media. However, this method oftentimes proves unsatisfactory because of the anaphylactic reactions induced in some hosts by the presence of foreign serum proteins in the vaccine. Further, blood serum is costly, and its inherent biological variability directly affects the performance of the culture medium.

Another attempt to detoxify a protein-free, Tween-containing nutrient medium is described in U.S. Pat. No. 3,816,261 which describes the introduction of a sufficient quantity of basic ion exchange resins to the nutrient medium. However, the presence of the highly ionic resins in the nutrient medium tends to limit the usefulness of this method. It seems that most of the virulent strains of Leptospira fail to propagate in the presence of basic ion exchange resins, thus limiting the widespread use of this process.

Further, in order to prepare a pharmaceutically acceptable vaccine, the basic ion exchange resins must be removed from the nutrient medium by complicated and time-consuming purification steps. Therefore, a great need still exists for the development of a process to produce a protein-free nutrient medium useful in the efficient growth of Leptospira.

The present invention is predicated upon our discovery of a simple and inexpensive procedure for producing a non-toxic, protein- and resin-free Leptospira nutrient medium for the large scale culture of Leptospira which allows the use of polysorbates as a source of fatty acid while totally eliminating the toxic side effects heretofore a characteristic of such sources.

Accordingly, a prime object of this invention is the preparation of a protein- and resin-free non-toxic nutrient medium for the propagation of Leptospira which contains as its primary principal components, detoxified polysorbate, preferred, but not limited to, Tween 20, 40, 60 and 80, as the fatty acid source, essential vitamins, inorganic salts and an organic buffer.

Another object of this invention is to produce a protein-free nutrient medium which will allow the large scale propagation of high cell yields of a wide variety of virulent strains of Leptospira.

Still another object of this invention is to produce a protein-free nutrient medium whereby subculture of pathogenic Leptospira can be attained.

Still another object of this invention is the provision of a method to remove the toxic impurities contained in the commercially available polysorbates so that such polysorbates, once detoxified pursuant hereto, can be used as a source of fatty acid in a Leptospira protein-free nutrient medium.

These and still further objects as shall hereinafter appear are fulfilled by the present invention in a remarkably unexpected fashion as will be readily discerned from the following detailed description of certain exemplary embodiments of this invention.

In the practice of the present invention, a protein-free non-toxic nutrient medium is prepared by first detoxifying a commercially available polysorbate source by engaging the polysorbate with about ½ to 6 parts by weight of activated charcoal which adsorbs substantially all of the aforesaid toxic impurities thereupon, separating the detoxified polysorbate from the charcoal, and thereafter under specific physical conditions, adding the detoxified polysorbate to other essential nutrient components, namely, vitamin $B_{12}$, vitamin $B_1$, a soluble manganese salt such as manganese sulfate, a soluble magnesium salt such as magnesium chloride, a soluble ammonium salt such as ammonium chloride, and an organic buffer having a $pK_{(a)}$ range between 6.1 and 8.3. Representative buffers which may be used in the medium include N-Tris(hydroxymethyl)methyl-2-aminoethane sulfonic acid (TES), N-2-hydroxyethylpiperazine-$N^1$-2-ethanesulfonic acid (HEPES), 2(N-Morpholino) ethane sulfonic acid (MES), N-(2-Acetamido) iminodiacetic acid (ADA), Piperazine-N,N'-bis(2-ethane sulfonic acid (PIPES), N-(2-Acetamido)-2-amino ethane sulfonic acid (ACES), N,N-Bis(2-hydroxyethyl)-2-amino ethane sulfonic acid (BES), 3-(N-Morpholino) propane sulfonic acid (MOPS), N-2-Hydroxyethyl Piperazine-N,-3-propane sulfonic acid (EPPS), Tris(hydroxymethyl) amino methane (TRIS), N-Tris(- hydroxymethyl) methyl glycine (TRICINE), N,N-Bis(2-hydroxyethyl) glycine (BICINE), and glycyl glycine. Other known nutrient components (e.g., calcium salts, iron salts, zinc salts, glycerol, potassium salts, etc.) may be added to the mixture to enhance the nutritional quality of the medium as will be later described.

In a commercial scale batch operation, it is often convenient and economically advantageous to prepare a concentrated nutrient medium of about 10 power, and thereafter to dilute this concentrate with distilled water to the proper level when it is used. In a representative operation, the 10 power concentrate is prepared by first producing a standard stock solution of each of the several components of the nutrient medium, and then combining each stock solution with the remaining components to form a nutrient medium of desired composition. Thus, in such a practice of the present invention, stock solutions of each of our preferred ingredients were prepared at 10 power as follows:

The polysorbate stock solution (e.g., Tween 20, 40, 60 and 80) for use in the invention was prepared by dissolving 20 grams of a preselected polysorbate (e.g., Tween 60) in about 200 ml distilled water at room temperature and stirring the solution until a substantially homogeneous consistency is obtained. While the aqueous solution is being stirred, approximately 40 g of activated charcoal (e.g., NORIT A available at J. T. Baker Co.) is added slowly. Although these represent preferred proportions of ingredients, the ratio of Tween to charcoal may range from 1:6 to 6:1 in sufficient water to facilitate intimate admixture and separation of charcoal without substantial loss of polysorbate. Stirring of the mixture is continued slowly for 1 to 72 hrs. at a temperature of between 0° to 121° C. and thereafter allowed to settle for a period of 1 to 72 hrs. at 0° to 121° C. Preferably the stirring and settling are carried out between about 4° and 37° C. Each polysorbate solution is then carefully decanted from the charcoal sediment, centrifuged at about 10,000 x gravity for about 1 hr. and thereafter subjected to thin channel ultrafiltration using a XM100 membrane (Amicon Co.) to remove any remaining charcoal fines from the polysorbate stock solution which may then be stored until needed.

The ammonium chloride ($NH_4Cl$) stock solution was prepared by dissolving 25.0 g of ammonium chloride into 100 ml of distilled water at room temperature and stored until needed.

A magnesium chloride and calcium chloride stock salt solution was prepared by dissolving 1.5 g of magnesium chloride ($MgCl_2.6H_2O$) and 1.5 g calcium chloride ($CaCl_2.H_2O$) into 100 ml of distilled water at room temperature and then stored until needed.

The manganese stock salt solution was prepared by dissolving between 0.1 and 10.0 g of manganese sulfate ($MnSO_4.H_2O$) into 100 ml of distilled water and thereafter stored until needed. Manganese is essential to the successful transfer of the organisms and secondary serial culture.

The vitamin $B_1$ stock solution was prepared by adding 0.5 g of thiamine hydrochloride into 100 ml distilled water, autoclaving, cooling to room temperature and thereafter stored until needed.

A vitamin $B_{12}$ stock solution was prepared by adding 0.02 g of cyanocobalamin to 100 ml of distilled water and thereafter stored until needed.

An optional iron salt stock solution was prepared by dissolving 0.1 g of ferrous sulfate ($FeSO_4.7H_2O$) into 100 ml of distilled water. The iron stock solution must be used while fresh.

An optional zinc salt stock solution was prepared by adding 0.1 g of zinc sulfate ($ZnSO_4.7H_2O$) into 100 ml of distilled water and thereafter stored until needed.

An optional glycerol stock solution was prepared by dissolving 10 g of glycerol into 100 ml of distilled water and thereafter stored until needed.

An optional potassium salt solution was prepared by dissolving 10 g of anhydrous potassium dihydrogenphosphate ($KH_2PO_4$) into 100 ml of distilled water and thereafter stored until needed.

The medium must not contain copper sulfate ($CuSO_4$).

Broadly stated, the composition of a typical 10X medium is approximately as follows:

|  | Parts by weight |
|---|---|
| Organic buffer | 0.6 to 50 |
| NaCl | 0.5 to 1.5 |
| Sodium pyruvate | 0.1 to 0.4 |
| Glycerol 10% stock solution | 0.5 to 2 |
| Detoxified polysorbate 10% stock solution | 1 to 40 |
| Calcium-magnesium salt 3% stock solution | 0.5 to 2 |
| Zinc salt 0.1% stock solution | 0.3 to 1 |
| Iron salt 0.1% stock solution | 0.3 to 1 |
| Vitamin $B_1$ 0.5% stock solution | 0.5 to 2 |
| Ammonium salt 25% stock solution | 0.5 to 1.5 |
| Vitamin $B_{12}$ 0.02% stock solution | 0.5 to 2 |
| Manganese salt 0.5 to 2% stock solution | 0.1 to 10 |
| Potassium salt 10% stock solution | 0.5 to 2 |
| (NaOH 1N to pH 6.5 to 8.5) | |
| Water to make | 100 |

Because the detoxified polysorbate is added as an approximately 10% solution, the 10X medium contains from about 0.1 to 4 parts by weight of polysorbate per 100 ml of medium equal to about 0.01% to 0.4% polysorbate per liter of 1X culture medium. Similarly, the other essential ingredients are present in the 10X medium in amounts as follows: ammonium salt about 0.125 to 0.375 parts by weight per 100 ml of medium, manganese salt about 0.0005 to 0.2 parts, magnesium salt about 0.0075 to 0.03 parts, vitamin $B_1$ about 0.0025 to 0.01 parts and vitamin $B_{12}$ about 0.0001 to 0.0004 parts.

The following examples describing certain embodiments of the invention, are presented to further aid in the understanding thereof and not by way of limitation.

EXAMPLE 1

Twenty grams of polysorbate (Tween 60) are dissolved in 200 ml distilled water and stirred. While this solution is being stirred, 40.0 g of activated charcoal (NORIT A — J. T. Baker Co.) is added slowly to the solution to insure the formation of a homogeneous suspension of charcoal particles. This mixture is then stirred slowly for 18 hrs. at 4° C. The polysorbate is then carefully decanted from the charcoal sediment, centrifuged (10,000 × g for 1 hr.) and filtered in a thin channel ultrafiltration unit using a XM100 membrane (Amicon Corp.) to remove any remaining charcoal therefrom.

EXAMPLE 2

A 10X protein-free medium, using HEPES as the organic buffer, is prepared as follows:

Each of the following ingredients are added slowly to 50 ml of distilled water while being stirred:

| | |
|---|---|
| HEPES | 1.2 g |
| NaCl | 0.9 g |
| Sodium pyruvate | 0.2 g |
| Glycerol stock solution | 1.0 ml |
| Modified Tween 60 stock solution | 12.0 ml |
| Modified Tween 40 stock solution | 3.0 ml |
| CaCl$_2$ . MgCl$_2$ stock solution | 1.0 ml |
| ZnSO$_4$ stock solution | 0.5 ml |
| FeSO$_4$ stock solution | 0.5 ml |
| Autoclaved thiamine stock solution | 1.0 ml |
| NH$_4$Cl stock solution | 0.9 ml |
| Cyanocobalamin stock solution | 1.0 ml |
| MnSO$_4$ stock solution | 1.0 ml |
| KH$_2$PO$_4$ stock solution | 1.0 ml |

After the above ingredients are combined, the pH of the medium is adjusted to 7.6 using 1 N NaOH. The volume of the medium is then brought to 100 ml by the addition of distilled water. The resulting 10X medium is sterilized by filtration. Thereafter, one volume of the 10X medium is added to 9 volumes of sterile distilled water to prepare the 1X protein-free medium. One of the modified Tween stock solutions (1 ml per 100 ml 1X medium) may be added periodically to the culture when it is in logarithmic phase of growth to increase the final cell yield.

EXAMPLE 3

A preparation of the 10X protein-free medium, using TES as the organic buffer, is prepared as follows:

Each of the following ingredients are added slowly to 50 ml of distilled water while it is stirred:

| | |
|---|---|
| TES | 10 g |
| NaCl | 0.9 g |
| Sodium pyruvate | 0.2 g |
| Glycerol stock solution | 1.0 ml |
| Modified Tween 60 stock solution | 12.0 ml |
| Modified Tween 40 stock solution | 3.0 ml |
| $CaCl_2 . MgCl_2$ stock solution | 1.0 ml |
| $ZnSO_4$ stock solution | 0.5 ml |
| $FeSO_4$ stock solution | 0.5 ml |
| Autoclaved thiamine stock solution | 1.0 ml |
| $NH_4Cl$ stock solution | 0.9 ml |
| Cyanocobalamin stock solution | 1.0 ml |
| $MnSO_4$ stock solution | 1.0 ml |
| $KH_2PO_4$ stock solution | 1.0 ml |

After the above ingredients are combined, the pH of the medium is adjusted to 7.6, using 1 N NaOH. The volume is then brought to 100 ml by the addition of distilled water. The resulting 10X medium is then sterilized by filtration. Thereafter, one volume of the sterilized 10X medium is added to 9 volumes of sterile distilled water to prepare the 1X protein-free medium. Modified Tween 80 (1 ml per 100 ml 1X medium) is added periodically to the culture when it is in logarithmic phase of growth to increase the final cell yield.

The protein-free medium supports the growth of leptospires to high cell yields. Examples of cell yields obtained with the five leptospiral serovars presently used in vaccine production are:

| | |
|---|---|
| canicola | $3.4 \times 10^9$ cells per ml |
| icterohaemorrhagiae | $3.2 \times 10^9$ cells per ml |
| pomona | $3.1 \times 10^9$ cells per ml |
| grippotyphosa | $2.6 \times 10^9$ cells per ml |
| hardjo | $3.4 \times 10^9$ cells per ml |

The generation time of leptospires cultivated in the protein-free medium is similar to that for leptospires grown in protein-containing media.

For maximum utility, the medium according to the present invention is prepared with an organic buffer. The avirulent strains of leptospires may be grown in a medium containing an inorganic buffer but the virulent strains *icterohaemorrhagiae* and *grippotyphosa* require an organic buffer of the class described.

Although the protein-free medium of the present invention was developed for the culturing of Leptospira organisms, it may be used for other purposes for which a protein containing component may be added. For example, it has been found that *grippotyphosa* organisms may be grown in protein-free media, but to enable transfer of the organisms to form secondary serial cultures, albumin must be present. Normally the medium should contain about 1% albumin. However, utilizing the protein-free medium of the present invention supplemented by the addition of as little as 0.1% albumin enables *grippotyphosa* organisms to be grown and transferred.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A protein-free nutrient medium, suitable for culture growth of Leptospira organisms, which comprises an aqueous solution of a buffer, mineral salts, vitamins and a detoxified charcoal treated polysorbate, said polysorbate being detoxified by admixture in aqueous solution with activated charcoal, followed by separation of the charcoal.

2. A medium according to claim 1 wherein said polysorbate is selected from the group consisting of polyalkylene derivatives of sorbitol monoesters of fatty acids having 12 to 20 carbon atoms.

3. A medium according to claim 1 wherein said polysorbate and charcoal are admixed in ratio between about 1:6 to 6:1.

4. A medium according to claim 1 wherein:

(A) said medium is a concentrate dilutable to one-tenth strength, (B) said buffer is present in amount between about 0.6 to 50 parts by weight per 100 parts medium, and (C) said detoxified polysorbate is present in amount between about 0.1 to 4 parts by weight per 100 parts medium.

5. A medium according to claim 4 wherein per 100 parts by weight of medium:

(A) a soluble manganese salt is present in amount between about 0.0005 to 0.2 parts by weight, (B) a soluble magnesium salt is present in amount between 0.0075 to 0.03 parts, (C) an ammonium salt is present in amount between about 0.125 to 0.375 parts, (D) vitamin $B_1$ is present in amount between about 0.0025 to 0.01 parts, and (E) vitamin $B_{12}$ is present in amount between about 0.0001 to 0.0004 parts.

6. A medium according to claim 1 wherein said buffer is an organic buffer having a $pK_{(a)}$ range between 6.1 and 8.3.

7. A method for preparing a protein-free nutrient medium, suitable for culture growth of leptospira organisms, which method comprises:

(A) admixing a polysorbate in aqueous solution with activated charcoal for a sufficient time to detoxify that polysorbate, (B) separating the polysorbate from the charcoal, and (C) combining the detoxified polysorbate in an aqueous solution of buffer, mineral salts and vitamins.

8. A method according to claim 7 wherein said polysorbate and charcoal are admixed in ratio between about 1:6 to 6:1.

9. A method according to claim 7 wherein said polysorbate and charcoal are admixed by stirring and said charcoal is separated by settling, followed by decantation, centrifugation and filtration.

10. A method according to claim 7 wherein said polysorbate is selected from the group consisting of polyalkylene derivatives of sorbitol monoesters of fatty acids having 12 to 20 carbon atoms.

11. A method according to claim 7 wherein:

(A) said medium is prepared as a concentrate dilutable to one tenth strength, (B) said buffer is combined in amount between about 0.6 to 50 parts by weight per 100 parts medium, and (C) said detoxified polysorbate is combined in amount between about 0.1 to 4 parts by weight per 100 parts medium.

12. A method according to claim 11 wherein, per 100 parts by weight of medium, (A) a soluble manganese salt is combined in amount between about 0.0005 to 0.2 parts by weight, (B) a soluble magnesium salt is combined in amount between about 0.0075 to 0.03 parts, (C) an ammonium salt is combined in amount between about 0.125 to 0.375 parts, (D) vitamin $B_1$ is combined in amount between about 0.0025 to 0.01 parts, and (E) vitamin $B_{12}$ is combined in amount between about 0.0001 to 0.0004 parts.

13. A method according to claim 7 wherein said buffer is an organic buffer having a $pK_{(a)}$ range between 6.1 and 8.3.

* * * * *